US008523630B2

(12) United States Patent
Bush

(10) Patent No.: US 8,523,630 B2
(45) Date of Patent: *Sep. 3, 2013

(54) DEVICE AND METHOD FOR IMMOBILIZING PATIENTS FOR BREAST RADIATION THERAPY

(75) Inventor: David A. Bush, Loma Linda, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/540,475

(22) Filed: Jul. 2, 2012

(65) Prior Publication Data

US 2012/0271095 A1    Oct. 25, 2012

Related U.S. Application Data

(63) Continuation of application No. 12/515,523, filed as application No. PCT/US2007/085309 on Nov. 20, 2007, now Pat. No. 8,210,899.

(60) Provisional application No. 60/866,814, filed on Nov. 21, 2006.

(51) Int. Cl.
*A41C 3/00* (2006.01)

(52) U.S. Cl.
USPC .................................. 450/36; 450/92; 450/93

(58) Field of Classification Search
USPC ............... 450/92, 93, 1, 39, 54–58, 36–38; 600/562–567, 411, 414, 417, 426, 427, 429, 600/439
See application file for complete search history.

(56) References Cited

U.S. PATENT DOCUMENTS

| 2,469,084 A | | 5/1949 | Schenker | |
|---|---|---|---|---|
| 2,580,264 A | * | 12/1951 | Wright et al. | 623/7 |
| 2,675,564 A | | 4/1954 | Hughes | |
| 3,145,240 A | * | 8/1964 | Proulx et al. | 264/53 |
| 3,397,411 A | | 8/1968 | Rossi | |
| 3,449,570 A | | 6/1969 | Kok | |
| 3,545,739 A | | 12/1970 | D'Avignon | |
| 3,556,455 A | | 1/1971 | Storm | |
| 3,604,931 A | | 9/1971 | Kastner et al. | |
| 3,640,787 A | | 2/1972 | Heller | |
| 3,689,949 A | | 9/1972 | Weinstein et al. | |

(Continued)

FOREIGN PATENT DOCUMENTS

| DE | 2513896 | 10/1975 |
|---|---|---|
| DE | 2833800 | 12/1979 |

(Continued)

OTHER PUBLICATIONS

"Dedicated Medical Ion Accelerator Design Study" by Lawrence Berkeley Laboratory, et al., Dec. 1977, PCTA008295-PCTA008455.

(Continued)

*Primary Examiner* — Gloria Hale
(74) *Attorney, Agent, or Firm* — Knobbe Martens Olson & Bear LLP

(57) ABSTRACT

According to the improved systems and methods described herein, a patient may be immobilized so that one or both breasts are returned to a known position. Additionally, the improved systems and methods reduce respiratory movement of the breasts. Thus, the immobilization devices and techniques described herein provide accurate and reproducible breast positioning while simultaneously reducing respiratory motion.

10 Claims, 6 Drawing Sheets

(56) References Cited

U.S. PATENT DOCUMENTS

| | | | |
|---|---|---|---|
| 3,745,998 A | | 7/1973 | Rose |
| 3,762,404 A | | 10/1973 | Sakita |
| 3,778,049 A | | 12/1973 | Viamonte, Jr. |
| 3,783,251 A | | 1/1974 | Pavkovich |
| 3,848,132 A | | 11/1974 | Foderaro |
| 3,851,644 A | | 12/1974 | Slagle |
| 3,852,610 A | | 12/1974 | Mcintyre |
| 3,885,258 A | | 5/1975 | Regan |
| 3,893,198 A | | 7/1975 | Blair |
| 3,897,345 A | | 7/1975 | Foster |
| 3,897,777 A | | 8/1975 | Morrison |
| 3,901,588 A | | 8/1975 | Longhenry |
| 3,905,054 A | | 9/1975 | Windsor et al. |
| 3,942,012 A | | 3/1976 | Boux |
| 3,947,686 A | | 3/1976 | Cooper et al. |
| 3,957,262 A | | 5/1976 | McReynolds |
| 3,986,697 A | | 10/1976 | Amor, Jr. et al. |
| 4,030,719 A | | 6/1977 | Gabriele et al. |
| 4,034,224 A | | 7/1977 | Heavens et al. |
| 4,064,401 A | | 12/1977 | Marden |
| 4,069,457 A | | 1/1978 | Martin et al. |
| 4,095,114 A | | 6/1978 | Taumann |
| 4,112,306 A | | 9/1978 | Nunan |
| 4,146,793 A | | 3/1979 | Bergstrom et al. |
| 4,190,772 A | | 2/1980 | Dinwiddie et al. |
| 4,206,355 A | | 6/1980 | Boux |
| 4,230,129 A | | 10/1980 | LeVeen |
| 4,250,137 A | * | 2/1981 | Riedler .................. 264/554 |
| 4,252,594 A | | 2/1981 | Cooper |
| 4,256,112 A | | 3/1981 | Kopf et al. |
| 4,262,204 A | | 4/1981 | Mirabella |
| 4,269,512 A | | 5/1981 | Nosler |
| 4,287,425 A | | 9/1981 | Elliot, Jr. |
| 4,327,046 A | | 4/1982 | Davis et al. |
| 4,347,213 A | | 8/1982 | Rogers, Jr. |
| 4,378,813 A | | 4/1983 | Lovelace et al. |
| 4,392,239 A | | 7/1983 | Wilkens |
| 4,400,820 A | | 8/1983 | O'Dell et al. |
| 4,401,492 A | * | 8/1983 | Pfrommer .................. 156/61 |
| 4,442,352 A | | 4/1984 | Brahme |
| 4,450,122 A | | 5/1984 | Gallina |
| 4,484,571 A | | 11/1984 | Velasquez |
| 4,504,050 A | | 3/1985 | Osborne |
| 4,552,508 A | | 11/1985 | Reid |
| 4,578,757 A | | 3/1986 | Stark |
| 4,591,341 A | | 5/1986 | Andrews |
| 4,600,551 A | * | 7/1986 | Erb .................. 264/222 |
| 4,616,814 A | | 10/1986 | Harwood-Nash et al. |
| 4,666,304 A | | 5/1987 | Davies |
| 4,671,284 A | | 6/1987 | Wilson et al. |
| 4,672,212 A | | 6/1987 | Brahme |
| 4,682,818 A | | 7/1987 | Morell |
| 4,688,780 A | | 8/1987 | Hanz |
| 4,705,955 A | | 11/1987 | Mileikowsky |
| 4,752,064 A | | 6/1988 | Voss |
| 4,779,858 A | | 10/1988 | Saussereau |
| 4,789,930 A | | 12/1988 | Sones et al. |
| 4,796,613 A | | 1/1989 | Heumann et al. |
| 4,812,658 A | | 3/1989 | Koehler |
| 4,815,448 A | | 3/1989 | Mills |
| 4,819,257 A | | 4/1989 | Grasser et al. |
| 4,841,965 A | | 6/1989 | Jacobs |
| 4,848,340 A | | 7/1989 | Bille et al. |
| 4,870,287 A | | 9/1989 | Cole et al. |
| 4,905,267 A | | 2/1990 | Miller et al. |
| 4,917,344 A | | 4/1990 | Prechter et al. |
| 4,926,457 A | | 5/1990 | Poehner et al. |
| 4,979,519 A | | 12/1990 | Chavarria et al. |
| 5,014,290 A | | 5/1991 | Moore et al. |
| 5,017,789 A | | 5/1991 | Young et al. |
| 5,037,374 A | | 8/1991 | Carol |
| 5,039,057 A | | 8/1991 | Prechter et al. |
| 5,039,867 A | | 8/1991 | Nishihara et al. |
| 5,046,708 A | | 9/1991 | Schaefer |
| 5,048,071 A | | 9/1991 | Van Steenburg |
| 5,049,147 A | | 9/1991 | Danon |
| 5,054,049 A | | 10/1991 | Manabe |
| 5,079,426 A | | 1/1992 | Antonuk et al. |
| 5,081,665 A | | 1/1992 | Kostich |
| 5,090,047 A | | 2/1992 | Angotti et al. |
| 5,094,241 A | | 3/1992 | Allen |
| 5,107,839 A | | 4/1992 | Houdek et al. |
| 5,117,829 A | | 6/1992 | Miller et al. |
| 5,156,166 A | | 10/1992 | Sebring |
| 5,168,514 A | | 12/1992 | Horton, Jr. et al. |
| 5,207,688 A | | 5/1993 | Carol |
| 5,240,218 A | | 8/1993 | Dye |
| 5,242,455 A | | 9/1993 | Skeens et al. |
| 5,269,305 A | | 12/1993 | Corol |
| 5,274,864 A | | 1/1994 | Morgan |
| 5,276,927 A | | 1/1994 | Day |
| 5,278,886 A | | 1/1994 | Ohgushi, et al. |
| 5,281,232 A | | 1/1994 | Hamilton et al. |
| 5,287,576 A | | 2/1994 | Fraser |
| 5,343,048 A | | 8/1994 | Pastyr |
| 5,361,765 A | | 11/1994 | Herlihy et al. |
| 5,370,117 A | | 12/1994 | McLaurin, Jr. |
| 5,370,118 A | | 12/1994 | Vij et al. |
| 5,380,336 A | | 1/1995 | Misko et al. |
| 5,382,914 A | | 1/1995 | Hamm et al. |
| 5,388,580 A | | 2/1995 | Sullivan et al. |
| 5,402,463 A | | 3/1995 | Umetani et al. |
| 5,427,097 A | | 6/1995 | Depp |
| 5,446,548 A | | 8/1995 | Gerig et al. |
| 5,454,993 A | | 10/1995 | Kostich |
| 5,464,411 A | | 11/1995 | Schulte et al. |
| 5,485,833 A | | 1/1996 | Dietz |
| 5,511,549 A | | 4/1996 | Legg et al. |
| 5,531,229 A | | 7/1996 | Dean et al. |
| 5,538,494 A | | 7/1996 | Matsuda |
| 5,549,616 A | | 8/1996 | Schulte |
| 5,566,681 A | | 10/1996 | Manwaring et al. |
| 5,570,409 A | | 10/1996 | Yamaguchi et al. |
| 5,588,430 A | | 12/1996 | Bova et al. |
| 5,595,191 A | | 1/1997 | Kirk |
| 5,596,619 A | | 1/1997 | Carol |
| 5,602,892 A | | 2/1997 | Llacer |
| 5,622,187 A | | 4/1997 | Carol |
| 5,675,851 A | | 10/1997 | Feathers |
| 5,676,673 A | | 10/1997 | Ferre et al. |
| 5,727,554 A | | 3/1998 | Kalend et al. |
| 5,745,545 A | | 4/1998 | Hughes |
| 5,751,781 A | | 5/1998 | Brown et al. |
| 5,769,779 A | | 6/1998 | Alderson |
| 5,771,512 A | | 6/1998 | Kurakake et al. |
| 5,775,337 A | | 7/1998 | Hauger et al. |
| 5,778,047 A | | 7/1998 | Mansfield et al. |
| 5,782,244 A | | 7/1998 | Kostich |
| 5,792,147 A | | 8/1998 | Evans et al. |
| 5,797,924 A | | 8/1998 | Schulte et al. |
| 5,800,352 A | | 9/1998 | Ferre et al. |
| 5,806,116 A | | 9/1998 | Oliver et al. |
| 5,820,444 A | * | 10/1998 | McGaughey .................. 450/70 |
| 5,820,553 A | | 10/1998 | Hughes |
| 5,823,192 A | | 10/1998 | Kalend et al. |
| 5,825,845 A | | 10/1998 | Blair et al. |
| 5,832,550 A | | 11/1998 | Hauger et al. |
| 5,847,403 A | | 12/1998 | Hughes et al. |
| 5,848,449 A | | 12/1998 | Hauger et al. |
| 5,851,182 A | | 12/1998 | Sahadevan |
| 5,865,832 A | | 2/1999 | Knopp et al. |
| 5,895,926 A | | 4/1999 | Britton et al. |
| 5,911,655 A | | 6/1999 | Brenneisen |
| 5,947,981 A | | 9/1999 | Cosman |
| 5,983,424 A | | 11/1999 | Näslund |
| 6,003,174 A | | 12/1999 | Kantrowitz et al. |
| 6,023,694 A | | 2/2000 | Kouchi et al. |
| 6,026,392 A | | 2/2000 | Kouchi et al. |
| 6,085,227 A | | 7/2000 | Edlund et al. |
| 6,104,779 A | | 8/2000 | Shepherd et al. |
| 6,118,848 A | | 9/2000 | Reiffel |
| 6,161,237 A | | 12/2000 | Tang et al. |
| 6,178,430 B1 | | 1/2001 | Cohen et al. |
| 6,195,578 B1 | | 2/2001 | Distler et al. |

| | | |
|---|---|---|
| 6,240,161 B1 | 5/2001 | Siochi |
| 6,275,564 B1 | 8/2001 | Ein-Gal |
| 6,279,579 B1 | 8/2001 | Riaziat et al. |
| 6,282,739 B1 | 9/2001 | Livingston |
| 6,308,353 B1 | 10/2001 | Van Steenburg |
| 6,316,776 B1 | 11/2001 | Hiramoto et al. |
| 6,325,758 B1 | 12/2001 | Carol et al. |
| 6,345,114 B1 | 2/2002 | Mackie et al. |
| 6,375,355 B1 | 4/2002 | Fortin |
| 6,376,846 B2 | 4/2002 | Livingston |
| 6,385,286 B1 | 5/2002 | Fitchard et al. |
| 6,405,072 B1 | 6/2002 | Cosman |
| 6,437,513 B1 | 8/2002 | Selzer et al. |
| 6,445,766 B1 | 9/2002 | Whitham |
| 6,446,286 B1 | 9/2002 | Karmalawy |
| 6,452,999 B1 | 9/2002 | Maida |
| 6,462,490 B1 | 10/2002 | Matsuda et al. |
| 6,462,553 B1 | 10/2002 | Badura |
| 6,466,813 B1 | 10/2002 | Shukla et al. |
| 6,473,490 B1 | 10/2002 | Siochi |
| 6,476,403 B1 | 11/2002 | Dolinskii et al. |
| 6,565,577 B2 | 5/2003 | Cosman |
| 6,577,707 B2 | 6/2003 | Siochi |
| 6,597,005 B1 | 7/2003 | Badura et al. |
| 6,598,275 B1 | 7/2003 | Kolody et al. |
| 6,600,164 B1 | 7/2003 | Badura et al. |
| 6,614,038 B1 | 9/2003 | Brand et al. |
| 6,621,889 B1 | 9/2003 | Mostafavi |
| 6,639,234 B1 | 10/2003 | Badura et al. |
| 6,650,930 B2 | 11/2003 | Ding |
| 6,662,036 B2 | 12/2003 | Cosman |
| 6,670,618 B1 | 12/2003 | Hartmann et al. |
| 6,677,597 B1 | 1/2004 | Haberer et al. |
| 6,683,318 B1 | 1/2004 | Haberer et al. |
| 6,690,965 B1 | 2/2004 | Riaziat et al. |
| 6,693,283 B2 | 2/2004 | Eickhoff et al. |
| 6,698,045 B1 | 3/2004 | Coppens et al. |
| 6,704,957 B2 | 3/2004 | Rhodes |
| 6,710,362 B2 | 3/2004 | Kraft et al. |
| 6,725,078 B2 | 4/2004 | Bucholz et al. |
| 6,730,921 B2 | 5/2004 | Kraft |
| 6,731,970 B2 | 5/2004 | Schlossbauer et al. |
| 6,736,831 B1 | 5/2004 | Hartmann et al. |
| 6,745,072 B1 | 6/2004 | Badura et al. |
| 6,754,299 B2 | 6/2004 | Patch |
| 6,757,355 B1 | 6/2004 | Siochi |
| 6,769,806 B2 | 8/2004 | Moyers |
| 6,774,383 B2 | 8/2004 | Norimine et al. |
| 6,777,700 B2 | 8/2004 | Yanagisawa et al. |
| 6,780,149 B1 | 8/2004 | Schulte |
| 6,792,078 B2 | 9/2004 | Kato et al. |
| 6,795,523 B2 | 9/2004 | Steinberg |
| 6,799,068 B1 | 9/2004 | Hartmann et al. |
| 6,803,591 B2 | 10/2004 | Muramatsu et al. |
| 6,804,548 B2 | 10/2004 | Takahashi et al. |
| 6,809,325 B2 | 10/2004 | Dahl et al. |
| 6,813,788 B2 | 11/2004 | Dinkler et al. |
| 6,814,694 B1 | 11/2004 | Pedroni |
| 6,839,404 B2 | 1/2005 | Clark et al. |
| 6,855,942 B2 | 2/2005 | Bechthold et al. |
| 6,859,741 B2 | 2/2005 | Haberer et al. |
| 6,891,177 B1 | 5/2005 | Kraft et al. |
| 7,011,447 B2 | 3/2006 | Moyers |
| 7,076,821 B2 | 7/2006 | DeMooy |
| 7,120,223 B2 | 10/2006 | Nafstadius |
| 7,142,634 B2 | 11/2006 | Engler et al. |
| 7,154,108 B2 | 12/2006 | Tadokoro et al. |
| 7,154,991 B2 | 12/2006 | Earnst et al. |
| 7,173,265 B2 | 2/2007 | Miller et al. |
| 7,199,382 B2 | 4/2007 | Rigney et al. |
| 7,280,633 B2 | 10/2007 | Cheng et al. |
| 7,301,162 B2 | 11/2007 | Matsuda et al. |
| 7,331,713 B2 | 2/2008 | Moyers |
| 7,348,579 B2 | 3/2008 | Pedroni |
| 7,372,053 B2 | 5/2008 | Yamashita et al. |
| 7,398,309 B2 | 7/2008 | Baumann et al. |
| 7,446,328 B2 | 11/2008 | Rigney et al. |
| 8,210,899 B2 * | 7/2012 | Bush .................. 450/54 |
| 2002/0027969 A1 | 3/2002 | Maida |
| 2002/0032378 A1 | 3/2002 | Henderson et al. |
| 2002/0051513 A1 | 5/2002 | Pugachev et al. |
| 2002/0065461 A1 | 5/2002 | Cosman |
| 2002/0077545 A1 | 6/2002 | Takahashi et al. |
| 2002/0095730 A1 | 7/2002 | Al-Kassim et al. |
| 2002/0120986 A1 | 9/2002 | Erbel et al. |
| 2002/0188194 A1 | 12/2002 | Cosman |
| 2002/0193685 A1 | 12/2002 | Mate et al. |
| 2003/0007601 A1 | 1/2003 | Jaffray et al. |
| 2003/0031301 A1 | 2/2003 | Longton et al. |
| 2003/0086527 A1 | 5/2003 | Speiser et al. |
| 2003/0095625 A1 | 5/2003 | Steinberg |
| 2003/0164459 A1 | 9/2003 | Schardt et al. |
| 2003/0183779 A1 | 10/2003 | Norimine et al. |
| 2004/0013414 A1 | 1/2004 | Karger et al. |
| 2004/0028188 A1 | 2/2004 | Amann et al. |
| 2004/0034438 A1 | 2/2004 | Uematsu |
| 2004/0034932 A1 | 2/2004 | Zacharopoulos et al. |
| 2004/0042583 A1 | 3/2004 | Wackerle et al. |
| 2004/0082856 A1 * | 4/2004 | Marmarelis .................. 600/437 |
| 2004/0098445 A1 | 5/2004 | Baumann et al. |
| 2004/0123388 A1 | 7/2004 | Coppens et al. |
| 2004/0136495 A1 | 7/2004 | Carlsson et al. |
| 2004/0155206 A1 | 8/2004 | Marchand et al. |
| 2004/0158145 A1 | 8/2004 | Ghelmansarai et al. |
| 2004/0174958 A1 | 9/2004 | Moriyama et al. |
| 2004/0184579 A1 | 9/2004 | Mihara et al. |
| 2004/0184583 A1 | 9/2004 | Nagamine et al. |
| 2005/0116175 A1 | 6/2005 | Haberer |
| 2005/0161618 A1 | 7/2005 | Pedroni |
| 2005/0281374 A1 | 12/2005 | Cheng et al. |
| 2006/0002511 A1 | 1/2006 | Miller et al. |
| 2006/0017022 A1 | 1/2006 | Rigney et al. |
| 2006/0183960 A1 * | 8/2006 | Sioshansi et al. .................. 600/3 |
| 2007/0039621 A1 | 2/2007 | Moyers |
| 2007/0093100 A1 | 4/2007 | Sommer |
| 2007/0158592 A1 | 7/2007 | Hiramoto et al. |
| 2007/0164230 A1 | 7/2007 | Rigney et al. |
| 2007/0262269 A1 | 11/2007 | Trbojevic |
| 2008/0005643 A1 | 1/2008 | Park et al. |
| 2008/0031414 A1 | 2/2008 | Coppens |
| 2008/0042076 A1 | 2/2008 | Miller et al. |
| 2008/0056434 A1 | 3/2008 | Grozinger et al. |
| 2008/0187097 A1 | 8/2008 | Cheng et al. |
| 2008/0189859 A1 | 8/2008 | Sloan et al. |
| 2008/0191142 A1 | 8/2008 | Pedroni |
| 2008/0192892 A1 | 8/2008 | Dilmanian et al. |
| 2008/0292053 A1 | 11/2008 | Marash et al. |
| 2008/0317216 A1 | 12/2008 | Lifshitz et al. |
| 2009/0067577 A1 | 3/2009 | Rigney et al. |
| 2009/0154645 A1 | 6/2009 | Lifshitz et al. |
| 2009/0168960 A1 | 7/2009 | Jongen et al. |
| 2009/0202045 A1 | 8/2009 | Guertin et al. |
| 2009/0217456 A1 | 9/2009 | Lempen et al. |
| 2009/0260636 A1 | 10/2009 | Markstroem |
| 2009/0304153 A1 | 12/2009 | Amelia et al. |
| 2009/0309046 A1 | 12/2009 | Balakin |
| 2009/0314960 A1 | 12/2009 | Balakin |

FOREIGN PATENT DOCUMENTS

| | | |
|---|---|---|
| DE | 4418216 | 11/1995 |
| DE | 19612091 | 3/1997 |
| EP | 019136 | 11/1980 |
| EP | 247449 | 12/1987 |
| EP | 283082 | 9/1988 |
| EP | 465590 | 1/1992 |
| EP | 986070 | 3/2000 |
| EP | 986071 | 3/2000 |
| EP | 1064881 | 1/2001 |
| EP | 1454653 | 9/2004 |
| EP | 1584353 | 10/2005 |
| EP | 1709994 | 10/2006 |
| EP | 1792595 | 6/2007 |
| EP | 1795229 | 6/2007 |
| EP | 1900392 | 3/2008 |
| EP | 1935453 | 6/2008 |
| FR | 2701391 | 8/1994 |
| GB | 0870225 | 6/1961 |
| GB | 2068700 | 8/1981 |

| | | |
|---|---|---|
| GB | 2213066 | 8/1989 |
| JP | 61194400 | 8/1986 |
| NL | 7309246 | 10/1974 |
| WO | WO 88/01848 | 3/1988 |
| WO | WO 90/11721 | 10/1990 |
| WO | WO 90/11723 | 10/1990 |
| WO | WO 95/08293 | 3/1995 |
| WO | WO 99/10137 | 3/1999 |
| WO | WO 00/16175 | 3/2000 |
| WO | WO 00/59575 | 10/2000 |
| WO | WO 01/00276 | 1/2001 |
| WO | WO 01/89625 | 11/2001 |
| WO | WO 02/63638 | 2/2002 |
| WO | WO 03/039212 | 5/2003 |
| WO | WO 03/053520 | 7/2003 |
| WO | WO 03/076016 | 9/2003 |
| WO | WO 2004/026401 | 4/2004 |
| WO | WO 2004/032781 | 4/2004 |
| WO | WO 2005/018734 | 3/2005 |
| WO | WO 2005/018735 | 3/2005 |
| WO | WO 2005/037167 | 4/2005 |
| WO | WO 2005/102453 | 11/2005 |
| WO | WO 2006/060886 | 6/2006 |
| WO | WO 2006/076545 | 7/2006 |
| WO | WO 2006/094533 | 9/2006 |
| WO | WO 2007/054140 | 5/2007 |
| WO | WO 2007/061426 | 5/2007 |
| WO | WO 2007/062788 | 6/2007 |
| WO | WO 2007/068066 | 6/2007 |
| WO | WO 2007/127970 | 11/2007 |
| WO | WO 2008/051358 | 5/2008 |
| WO | WO 2008/064271 | 5/2008 |
| WO | WO 2008/081480 | 7/2008 |
| WO | WO 2008/142695 | 11/2008 |
| WO | WO 2009/129847 | 10/2009 |
| WO | WO 2009/142544 | 11/2009 |
| WO | WO 2009/142545 | 11/2009 |
| WO | WO 2009/142546 | 11/2009 |
| WO | WO 2009/142548 | 11/2009 |
| WO | WO 2009/142549 | 11/2009 |

OTHER PUBLICATIONS

"Design of a Proton Therapy Synchrotron" by Fermi National Accelerator Laboratory, Jun. 1986, LL467-LL574.
"Proceedings of a Medical Workshop on Accelerators for Charged-Particle Beam Therapy" by Fermilab, Jan. 1985, LL33170-LL33313.
"Product Overview" by BrainLAB Radiotherapy Solutions, Copyright 2004 BrainLABAG.
"Proton Therapy Facility: Engineering Design Report" by Fermi National Accelerator Laboratory, Feb. 1987, LL45441-LL45570.
"Proton Therapy System" by Brobeck Corporation, Nov. 1985, LL54413-LL54459.
Baglan, et al., "Accelerated Partial Breast Irradiation Using 3D Conformal Radiation Therapy (3D-CRT)" n. Engl. J. Med., vol. 55, No. 2, pp. 302-311, 2003.
Baglan, et al., "The Use of High-Dose-Rate Brachytherapy Alone After Lumpectomy in Patients with Early-Stage Breast Cancer Treated with Breast-Conserving Therapy" Int. J. Radiation Oncology Biol. Phys., vol. 50, No. 4, pp. 1003-1011, 2001.
Crile et al., "Factors Influencing Local Recurrence of Cancer After Partial Mastectomy" Cleveland Clinic Journal of Medicine, vol. 57, No. 2, pp. 143-146, Mar.-Apr. 1990.
Extended European Search Report for EP Application No. 07871543.0, mailed on May 4, 2012 in 9 pages.
Fisher, et al., "Twenty-Year Follow-Up of a Randomized Trial Comparing Total Mastectomy, Lumpectomy, and Lumpectomy Plus Irradiation for the Treatment of Invasive Breast Cancer" N Engl. J. Med., vol. 347, No. 16, pp. 1233-1241, Oct. 17, 2002.
Fisher, et al., "Conservative Surgery for the Management of Invasive and Noninvasive Carcinoma of the Breast: NSABP Trials" World J. Surg. 18, pp. 63-69, 1994.
Fisher, et al., "Pathologic Findings from the National Surgical Adjuvant Breast Project (Protocol 6)" A Journal of American Cancer Society, vol. 57, No. 9, pp. 1717-1724, May 1, 1986.
Formenti, et al., "T1 Stage Breast Cancer: Adjuvant Hypofractionated Conformal Radiation Therapy to Tumor Bed in Selected Postmenopausal Breast Cancer Patients-Pilot Feasibility Study[1]" Radiation Oncology, vol. 222, No. 1, pp. 172-178, Jan. 2002.
King, et al., "Long-Term Results of Wide-Field Brachytherapy as the Sole Method of Radiation Therapy after Segmental Mastectomy for $T_{is,1,2}$ Breast Cancer" The American Journal of Surgery, vol. 180, pp. 299-304, Oct. 2000.
Krishnan, et al., "Breast Conservation Therapy with Tumor Bed Irradiation Alone with a Selected Group of Patients with Stage I Breast Cancer" The Breast Journal, vol. 7, No. 2, pp. 91-96, 2001.
Liljegren, et al., "Sector Resection With or Without Postoperative Radiotherapy for Stage I Breast Cancer: Five-Year Results of a Randomized Trial[1]" Journal of the National Cancer Institute, vol. 86, No. 9, pp. 717-722, May 4, 1994.
Miller, Daniel W. "Review of Proton Beam Radiation Therapy" Medical Physics, vol. 22, No. 11, Pt. 2, pp. 1943-1954, Nov. 1995.
Perera, et al. "Method of Localization and Implantation of the Lumpectomy Site for High Dose Rate Brachytherapy after Conservative Surgery for T1 and T2 Breast Cancer" Int. J. Radiation Oncology Biol. Phys., vol. 31, No. 4, pp. 959-965, 1995.
Perera, et al. "Local Resection and Brachytherapy Confined to the Lumpectomy Site for Early Breast Cancer: A Pilot Study" Journal of Surgical Oncology, vol. 65, No. 4, pp. 263-268, Aug. 1997.
Polgar, et al. "Sole Brachytherapy of the Tumor Bed After Conservative Surgery for T1 Breast Cancer: Five-Year Results of a Phase I-II Study and Initial Findings of a Randomized Phase III Trial" Journal of Surgical Oncology, vol. 80, Issue 3, pp. 121-128, Jul. 2002.
Poti, et al., "Partial Breast Irradiation with Interstitial $^{60}$Co Brachytherapy Results in Frequent Grade 3 or 4 Toxicity. Evidence Based On A 12-Year Follow-Up of 70 Patients" Int. J. Radiation Oncology Biol. Phys., vol. 58, No. 4, pp. 1022-1033, 2004.
Schmidt-Ullrich, et al. "Breast Conservation Therapy for Early Stage Breast Carcinoma with Outstanding 10-Year Locoregional Control Rates: A Case for Aggressive Therapy to the Tumor Bearing Quadrant" Int. J. Radiation Oncology Biol. Phys., vol. 27, pp. 545-552, 1993.
Urano, et al., "Relative Biological Effectiveness of Modulated Proton Beams in Various Murine Tissues" Int. J. Radiation Oncology Biol. Phys., vol. 10, No. 4, pp. 509-514, 1984.
Vaidya, et al. "Targeted Intra-Operative Radiotherapy (Targit): An Innovative Method of Treatment for Early Breast Cancer" Annals of Oncology, vol. 12, pp. 1075-1080, 2001.
Veronesi, et al. "Twenty-Year Follow-Up Of A Randomized Study Comparing Breast-Conserving Surgery With Radical Mastectomy for Early Breast Cancer" N. Engl. J. Med., vol. 347, No. 16, pp. 1227-1232, Oct. 17, 2002.
Veronesi, et al. "A Preliminary Report of Intraoperative Radiotherapy (IORT) in Limited-Stage Breast Cancers that are Conservatively Treated" European Journal of Cancer 37, pp. 2178-2183, 2001.
Vicini, et al. "Accelerated Treatment of Breast Cancer" Journal of Clinical Oncology, vol. 19, No. 7, pp. 1993-2001, Apr. 1, 2001.
Wazer, et al., "Preliminary Results of a Phase I/II Study of HDR Brachytherapy Alone for T1/T2 Breast Cancer" Int. J. Radiation Oncology Biol. Phys., vol.. 50, No. 4, pp. 889-897, 2002.
Wazer, et al., "Clinically Evident Fat Necrosis in Women Treated with High-Dose-Rate Brachytherapy Alone for Early-Stage Breast Cancer" Int. J. Radiation Oncology Biol. Phys., vol. 50, No. 1, pp. 107-111, 2001.
Whelan, et al. "Ipsilateral Breast Tumor Recurrence Postlumpectomy is Predictive of Subsequent Mortality: Results from a Randomized Trial" Int. J. Radiation Oncology Biol. Phys., vol. 30, pp. 11-16, 1994.

* cited by examiner

_US 8,523,630 B2_

DEVICE AND METHOD FOR IMMOBILIZING PATIENTS FOR BREAST RADIATION THERAPY

CROSS-REFERENCE TO RELATED APPLICATIONS

This application is a continuation of U.S. National Phase patent application Ser. No. 12/515,523, filed May 19, 2009, soon to issue as U.S. Pat. No. 8,210,899, which claims priority to International Application No. PCT/US2007/085309, filed Nov. 20, 2007, designating the United States of America and published in the English language, which claims priority to U.S. Provisional Patent Application No. 60/866,814, filed Nov. 21, 2006. The entire disclosures of each of the above-referenced applications are hereby expressly incorporated herein by reference for all that each contains.

BACKGROUND OF THE INVENTION

1. Field of the Invention

The present invention relates to devices and methods of immobilizing patients for radiation therapy.

2. Description of the Related Art

Whole breast radiotherapy is a treatment that may follow local excision (lumpectomy) of invasive breast cancer. One rationale for adjuvant radiotherapy is to reduce the recurrence rate of the breast cancer by eliminating residual foci of cancer in the region of the primary tumor as well as presumed occult multicentric disease in remote areas of the breast. However, the majority of cancer recurrences in the same breast after breast radiation therapy are in the same quadrant as the initial tumor. In fact, some 80-90% of breast cancer recurrences after breast radiation therapy occur in the immediate vicinity of the lumpectomy scar. Accordingly, treatment directed more specifically at the region of the breast involved with cancer may be equally efficacious in minimizing breast recurrence.

SUMMARY OF THE INVENTION

Neither this summary nor the following detailed description purports to define the invention. The invention is defined by the claims.

In one embodiment, a method of forming a support structure for immobilizing a patient in a prone position for delivery of radiation to at least one breast of the patient comprises positioning a support brassier on the patient, the support brassier comprising a semi-rigid cup sized to engage a breast of the patient, positioning the patient in a prone position in a support structure so that the cup is proximate to, but not in contact with, a bottom surface of the support structure. The method further comprises placing a malleable substance around the cup so that the substance substantially occupies a space between the bottom surface of the support structure and the cup with the patient positioned in the support structure and hardening the malleable substance that is placed around the cup so that the malleable substance becomes a substantially rigid breast immobilization device comprising contours corresponding with the cup.

In one embodiment, a device for immobilizing a patient for delivery of radiation to a breast of the patient comprises a support structure for supporting a patient in a prone position and a breast immobilization device comprising contours that substantially define a negative relief image of a cup that is fitted over a breast of the patient, the breast immobilization device being positioned within the support structure so that the cup engages and is supported by the breast immobilization device.

In one embodiment, a method of immobilizing a patient for radiation therapy to the patient's chest comprises positioning a breast immobilization device within a support structure, the breast immobilization device comprising contours that are custom-fit to engage with at least one of a patient's breasts and positioning the patient in a prone position on the support structure so that the at least one breast engages with the contours of the support structure.

In one embodiment, a device for immobilizing a patient for delivery of radiation to a breast of the patient comprises means for supporting a patient in a prone position and means for immobilizing a breast of the patient during delivery of radiation to the breast, the immobilization means being supported by the supporting means, wherein the immobilization means is configured to reproducibly position the breast for each of a plurality of radiotherapy treatments.

DETAILED DESCRIPTION OF THE PREFERRED EMBODIMENTS

Embodiments of the invention will now be described with reference to the accompanying Figures, wherein like numerals refer to like elements throughout The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
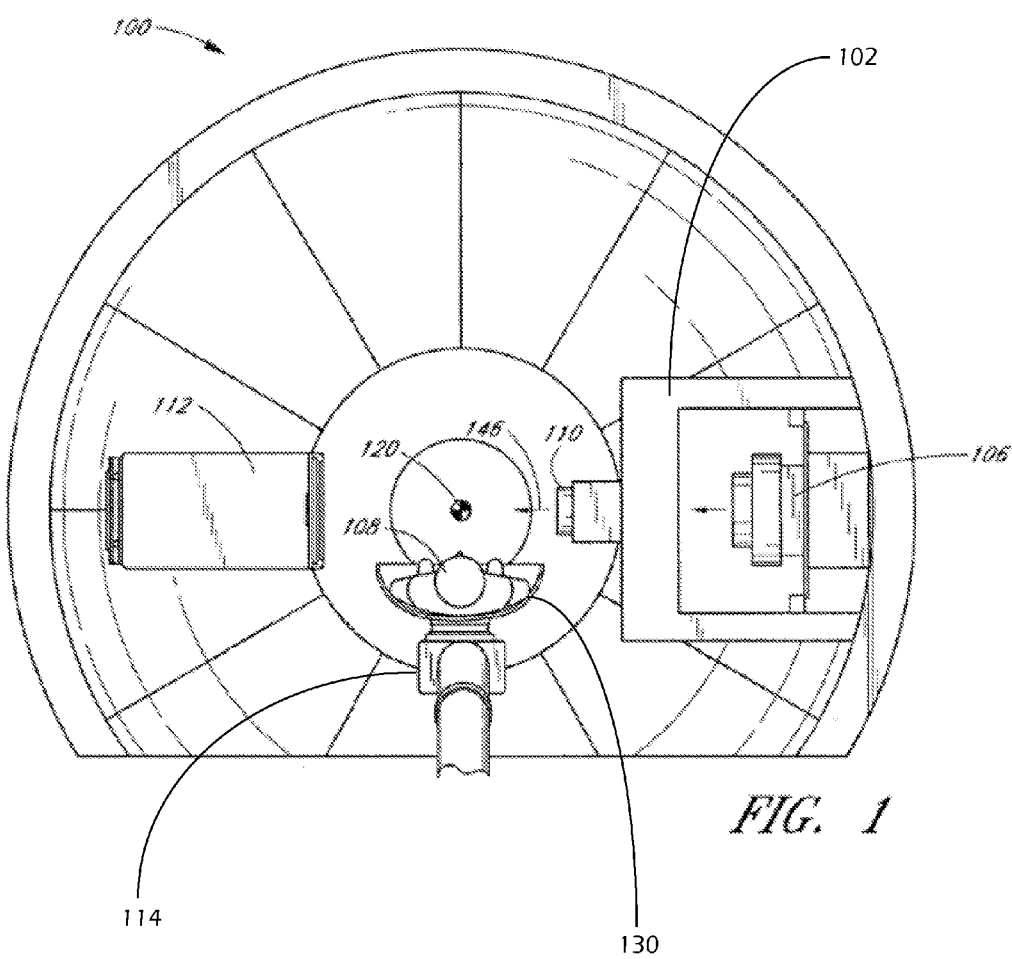
FIG. 1 is a side view of one embodiment of a radiation therapy system.

FIG. 1 is a side view of one embodiment of a radiation therapy system 100. The exemplary radiation therapy system 100 is designed to deliver therapeutic radiation doses to a target region within a patient 108, such as a cancer patient 108, for treatment of malignant or other conditions from one or more angles or orientations with respect to the patient 108.

In one embodiment, the radiation therapy system 100 is designed to deliver therapeutic doses of proton beams to a target area within the patient. Additional details on the structure and operation of such a proton radiation system can be found in U.S. Pat. No. 4,870,287, titled MULTI-STATION PROTON BEAM THERAPY SYSTEM, which is incorporated herein in its entirety by reference. In other embodiments, the system 100 is designed to deliver any other clinically suitable form of radiation known in the art, such as, for example, x-rays, gamma rays, hadrons, neutrons, etc.

In certain embodiments, the radiation therapy system 100 may include a patient treatment station and a gantry 102 which includes a generally hemispherical or frustoconical support frame for attachment and support of other components of the radiation therapy system 100. Additional details on the structure and operation of the gantry 102 can be found in U.S. Pat. Nos. 4,917,344 and 5,039,057, both titled ROLLER-SUPPORTED, MODULAR, ISOCENTRIC GENTRY AND METHOD OF ASSEMBLY, which are each incorporated by reference in their entireties.

The exemplary system 100 also comprises a nozzle 110 which is attached and supported by the gantry 102 such that the nozzle 110 may revolve relatively precisely about a gantry isocenter 120. The system 100 comprises a radiation source 106 delivering a therapeutic beam, such as a beam of accelerated protons, which pass through and are shaped by an aperture positioned on a distal end of the nozzle 110. An exemplary beam path is represented by numeral 146. In one embodiment, the aperture may be adjusted according to a patient's particular prescription of therapeutic radiation therapy. In other embodiments, alternative gantry configuration may be used in order to direct a radiation beam towards the patient 108.

In the embodiment of FIG. 1, the system 100 also comprises one or more imagers 112 which, in this embodiment, are retractable with respect to the gantry 102 between an extended position and a retracted position. In the illustration of FIG. 1, the imager 112 is shown in the extended position. In one embodiment, the imager 112 comprises a solid-state amorphous silicon x-ray imager which can develop image information such as from incident x-ray radiation that has passed through a patient's body. The system 100 may also comprises an x-ray source configured to emit appropriate x-ray radiation which passes through interposed patient tissue so as to generate a radiographic image of the interposed materials via the imager 112. The retractable aspect of the imager 112 provides the advantage of withdrawing the imager screen from the beam path of the radiation source 106 when the imager 112 is not needed thereby providing additional clearance within the gantry 102 enclosure as well as placing the imager 112 out of the path of potentially harmful emissions from the radiation source 102 thereby reducing the need for shielding to be provided to the imager 112. In this embodiment, the imagers and radiation sources 130 are arranged orthogonally to provide radiographic images of the patient from two directions.

The exemplary system 100 also comprises a patient positioner 114 and a patient support structure 130, also referred to as a pod 130, attached to the patient positioner 114. In one embodiment, the patient positioner 114 is adapted to, upon receipt of appropriate movement commands, position the patient support structure 130 in multiple translational and rotational axes and may be capable of positioning the patient support structure 130 in three orthogonal translational axes (e.g., longitudinal, vertical, and lateral) as well as three orthogonal rotational axes (e.g., pitch, roll, and yaw) so as to provide a full six degrees freedom of motion to placement of the patient support structure 130. In the illustration of FIG. 1, a patient is positioned in a supine (face-up) position on the support structure 130.

In certain embodiments, such as will be described in further detail below, an immobilization device may be positioned in the support structure 130 and shaped to interface with the contours of a specific patient's body. Thus, in the embodiment of FIG. 1, an immobilization device may be inserted between the support structure 130 and the patient 108. In one embodiment, the immobilization device comprises one or more beanbags or foam bead cushions, such as the VAC-LOK™ foam bead cushions manufactured by Med-Tec, Inc. In another embodiment, the immobilization device comprises a two-part expandable foam, such as one or more foam products manufactured by Med-Tec, Inc, quick setting polymeric foam, or other suitable immobilization substances. In other embodiments, the immobilization device comprises pillows, cushions, and/or bean-bags, for example. The use of an immobilization device that is formed to engage the contours of a patients body may advantageously reduce the patient's movement, allowing the radiation treatment plan to reduce an amount of tissue surrounding a target area that is irradiated.

While the following description periodically refers to the patient positioning system 100, the improved devices and methods described herein are usable with various other patient positioning systems. For example, the devices and methods described herein are usable with other automatic, semi-automatic, manual controlled with direct interface to the positioner controller, or fully manual (e.g., releasing a brake and moving each device axis with a hand crank), positioning systems. Thus, the systems and methods discussed herein are suitable for use with any other radiotherapy treatment devices and facilities.

The radiation system 100 may be used to deliver radiation treatment to any portion of a patient, including a patient's breast or breasts. While the system 100 may be used to provide whole breast radiation to the patient, systems and methods that provide partial breast radiotherapy, thereby reducing the negative effects of radiation on the entire breast, may provide effective adjuvant radiotherapy to a cancer (or other treatment) region in a patient's breast, while minimizing recurrence of cancer in the treated breast. More particularly, by confining treatment to a limited volume of breast tissue adjacent to the treatment region of the breast, such as a lumpectomy cavity, the amount of normal tissue exposed to radiotherapy can be reduced, potentially reducing acute and chronic toxicity. In addition, the smaller target volumes may allow use of hypofractionated treatment schedules, which decrease the time and inconvenience of breast conservation therapy, possibly minimizing scheduling problems with systemic chemotherapy, and potentially improving outcome by reducing delay to local therapy. Partial-breast radiation therapy may include post-operative interstitial brachytherapy, intracavitary brachytherapy to lumpectomy cavity, and/or external beam radiotherapy with photons utilizing 3-D conformal techniques, for example, among other known or later developed techniques.

Proton therapy may possess characteristics that prove useful for performing partial breast irradiation. In comparison to three-dimensional conformal radiation therapy with x-rays, the inherently superior depth dose characteristics (Bragg peak) minimizes the integral dose delivered to surrounding normal tissues, particularly the lung, heart, chest wall and treatment breast. For example, the physical properties of proton beams allow precise beam stopping within tissue at any given depth and shape, which may allow a reduction in an integral dose delivered to normal tissues. Furthermore, this allows highly conformal doses to be delivered with a very uniform dose distribution, eliminating "hot spots" from within the treatment region. Additionally, proton therapy is non-invasive and does not require disruptions to the skin of the breast, which may lead to an improved cosmetic outcome. Accordingly, immobilization devices and methods described herein may be used in conjunction with proton therapy planning and delivery, as well as any other type of radiation planning and delivery devices.

As those of skill in the art will recognize, the level of immobilization of a patient and, more specifically, of a treatment region of the patient, is determined based at least partly on a size of the treatment region that is irradiated. For example, if a patient is completely immobilized so that there is no movement of the treatment region, irradiation may be targeted to only the treatment region without including any of the surrounding tissue in the treatment plan. Thus, an irradiation area in a partial breast treatment plan may be reduced through improved immobilization of the breast.

Depending on the patient, the breasts move from a little to a lot as the patient breathes. Accordingly, even if the treatment breast is immobilized, there is still a certain amount of movement of the breast due to movement of the patient's lungs caused by normal breathing. Accordingly, the treatment region of a breast may be further reduced if movement of the breasts can be reduced.

According to the improved systems and methods described herein, a patient may be immobilized so that a treatment breast is accurately returned to a known position for each radiotherapy treatment. Additionally, the improved systems and methods reduce respiratory movement of the breasts. Thus, the immobilization devices and techniques described herein provide accurate and reproducible breast positioning while simultaneously eliminating respiratory motion. By providing accurately repeatable breast positioning, as well as reduction in respiratory motion, the systems and methods described herein allow treatment of a reduced treatment region of the patient's breast.

Figure 2A:
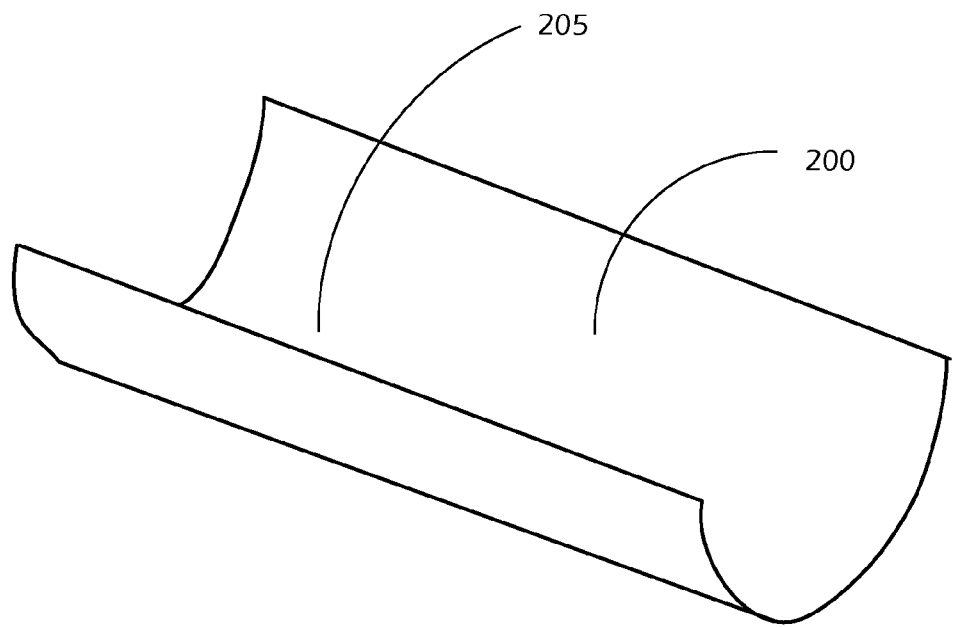
FIG. 2A is an isometric drawing of an exemplary patient support structure.
Figure 2B:
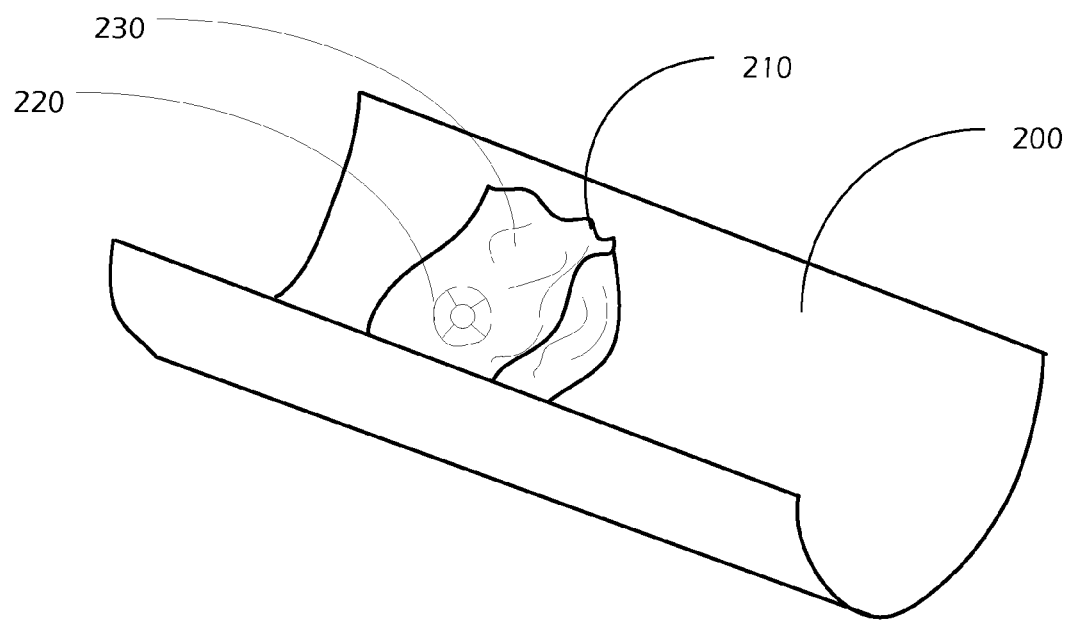
FIG. 2B is an isometric drawing of a breast immobilization device in the support structure of FIG. 2A, where the breast immobilization device is configured for immobilizing a left breast of a patient for radiation treatment

FIG. 2A is an isometric drawing of an exemplary patient support structure 200 and FIG. 2B is an isometric drawing of a breast immobilization device 210 in the support structure 200, where the breast immobilization device 210 is configured for immobilizing a left breast of a patient for radiation treatment.

In the embodiment of FIGS. 2A and 2B the breast immobilization device 210 comprises two-part expandable foam that has been hardened around a portion of a patient in a prone (face-down) position. For example, the patient may be positioned in the support structure 200 with a slight gap between the breasts and a bottom surface 205 of the support structure 200. The two-part foam may then be poured, or otherwise placed, around the chest region of the patient and allowed to harden around the breasts so that the contours of the breasts are mirrored in negative relief in the hardened foam. Accordingly, the patient's breasts may be more fully supported by the contoured breast immobilization device 210 compared to only the support structure 200, for example. Additionally, because the immobilization device 210 is fitted with the patient in the prone position, respiratory movement of the treatment breast is minimized when compared to respiratory movement that is experienced when a patient is in the supine position. Thus, the breast immobilization device not only allows the patient to be reproducibly positioned within the support structure 200 using the custom-molded immobilization device 210, but the prone positioned patient exhibits less respiratory movement of the treatment breast.

In one embodiment, prior to forming the breast immobilization device 210, the patient's shoulders, abdomen, and/or pelvis are supported by pillows, beanbags, foam structures, such as foam bead vacuum cushions, and/or other support structures. In this embodiment, when the patient is properly positioned on the foam bead vacuum cushions, for example, an opening around the chest area is formed, which may be filled with two-part expandable foam, for example, in order to form the breast immobilization device 210. In one embodiment, the air may be removed from the vacuum cushions prior to placement of the two-part foam around the chest area, in order to provide a substantially rigid immobilization for the head, shoulder, abdomen, and/or pelvis areas, while leaving an open space between the breasts and the support surface 200. Thus, after formation of the immobilization device 210 around the patient's chest area, the support structure 200 is filled with one or more pillows, beanbags, or foam structures that support the legs, head, and arms of the patient while the chest area of the patient is supported by a breast immobilization device 210 comprising expandable foam, or like material. In one embodiment, the breast immobilization device 210 may be formed of one or more foam bead vacuum cushions or other materials that suitably conform to the contours of a patient's breast(s) and provide a rigid or semi-rigid support structure.

Figure 3A:
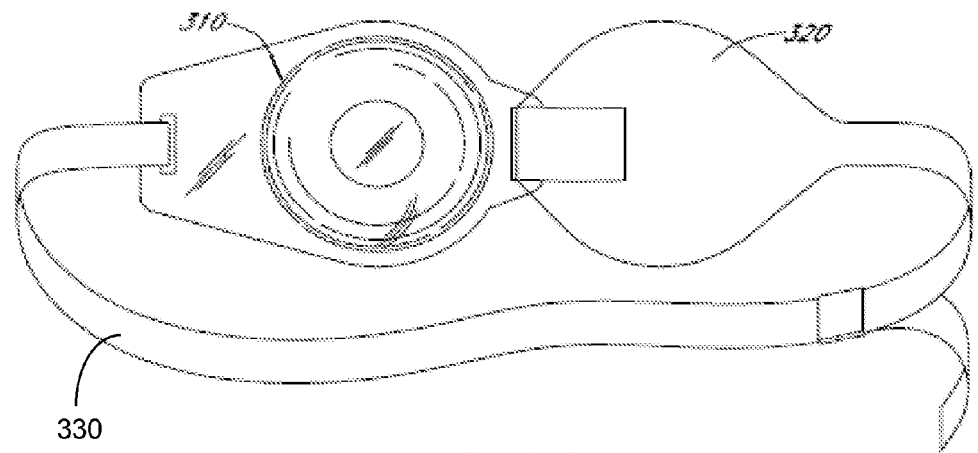
FIG. 3A illustrates an exemplary support brassier that comprises a cup for supporting a breast that will receive radiation treatment.
Figure 3B:
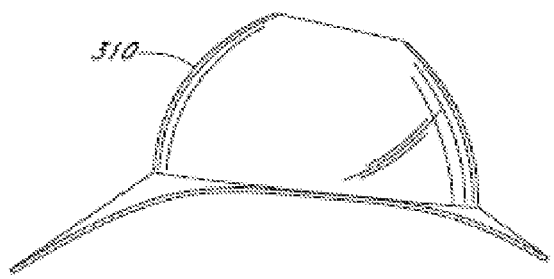
FIG. 3B is a side view of an exemplary cup that may be used to support a breast.

FIG. 3A illustrates an exemplary support brassier 300 that comprises a cup 310 for supporting a treatment breast of a radiotherapy patient. In one embodiment, the patient wears the support brassier 300 in order to further immobilize the treatment breast and/or repeatedly reposition the treatment breast in a substantially similar position. In one embodiment, the cup 310 is formed of rigid or semi-rigid material, such as plastic. In certain embodiments, the cup 310 may be replaced with other cups of various sizes in accordance with a breast size of the patient. For example, a series of cups may be interchangeably attached to the strap 330 so that cup sizes corresponding to varying breast sizes are available. In one embodiment, the cup 310 is configured to position the treatment breast in a reproducible shape. FIG. 3B is a side view of the exemplary cup 310.

In the embodiment of FIG. 3A, the support brassier 300 also comprises a compression material 320 that covers a breast that will not receive radiation treatment, which is referred to herein as the "contralateral breast." Radiation treatment plans typically attempt to reduce radiation that is delivered to areas outside of the radiation treatment region, such as the contralateral breast that is not intended to receive radiation treatment. Thus, the compression material 320 advantageously compresses the contralateral breast and positions the compressed breast further from a path of the radiation beam that is delivered to the treatment breast that is positioned in the cup 310. In one embodiment, the compression material 320 comprises cloth that is sufficiently strong to significantly flatten the contralateral breast under the compression material 320 when the support brassier 300 is tightened around the patient. In certain embodiments, the support brassier 300 may comprise two support cups, such as cup 310, to support both breasts of a patient in reproducible positions. In other embodiments, the cup 310 may be removed from the brassier 300, such as in the illustration of FIG. 3B, and be coupled with the two-part foam so that the patient's treatment breast engages the cup only when two-part foam is adjacent the patient.

With reference again to FIG. 2B, the breast immobilization device 210 is shown with a breast contour 220 that corresponds with a shape of the cup 310. In this embodiment, the patient was fitted with a support brassier having a cup 310 over the left breast so that when the breast immobilization device 210 was formed, the shape of the cup 310 was mirrored in the immobilization device 210. As illustrated in FIG. 2C, at position 230 of the breast immobilization device 210 there is only a very shallow cavity in the immobilization device due to the compression material 320 that was placed over the patient's right breast. Thus, in the embodiment of FIG. 2C, the patient may be immobilized for radiation treatment to the left breast in a manner that is further described below.

Figure 4:
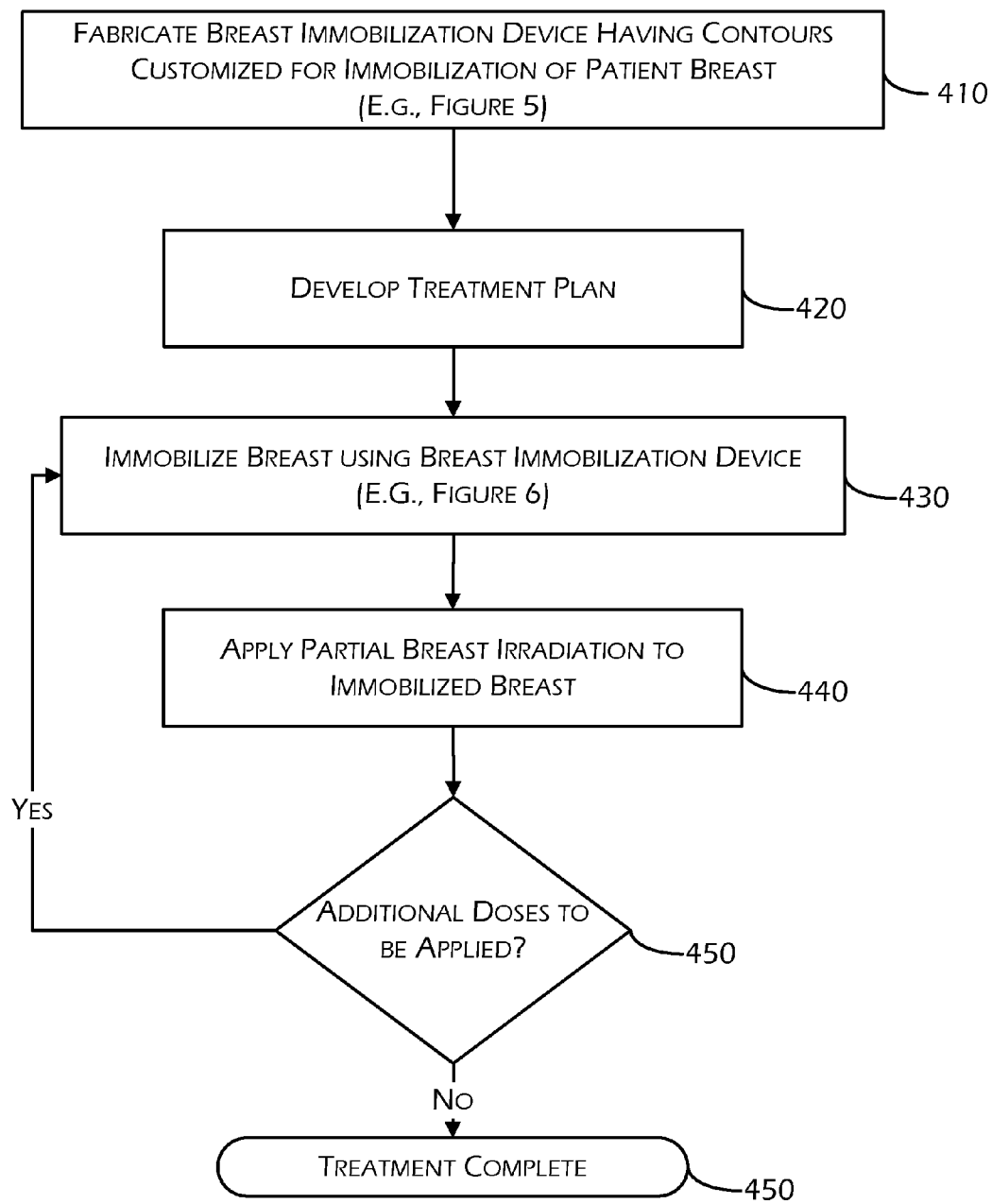
FIG. 4 is a flowchart illustrating an exemplary method of fabricating a breast immobilization device and using the immobilization device in repeatedly immobilizing a patient for radiation therapy.

FIG. 4 is a flowchart illustrating one embodiment of a method of fabricating a breast immobilization device and immobilizing a patient for partial breast radiation therapy. The exemplary method of FIG. 4 advantageously provides accurate and reproducible breast positioning while simultaneously reducing respiratory motion. The method of FIG. 4 may be used in conjunction with any type of radiation treatment, or other treatment to the breasts, such as full or partial breast radiation. Depending on the embodiment, the method of FIG. 4 may include fewer or additional blocks and the method may be performed in a different order.

Figure 5:
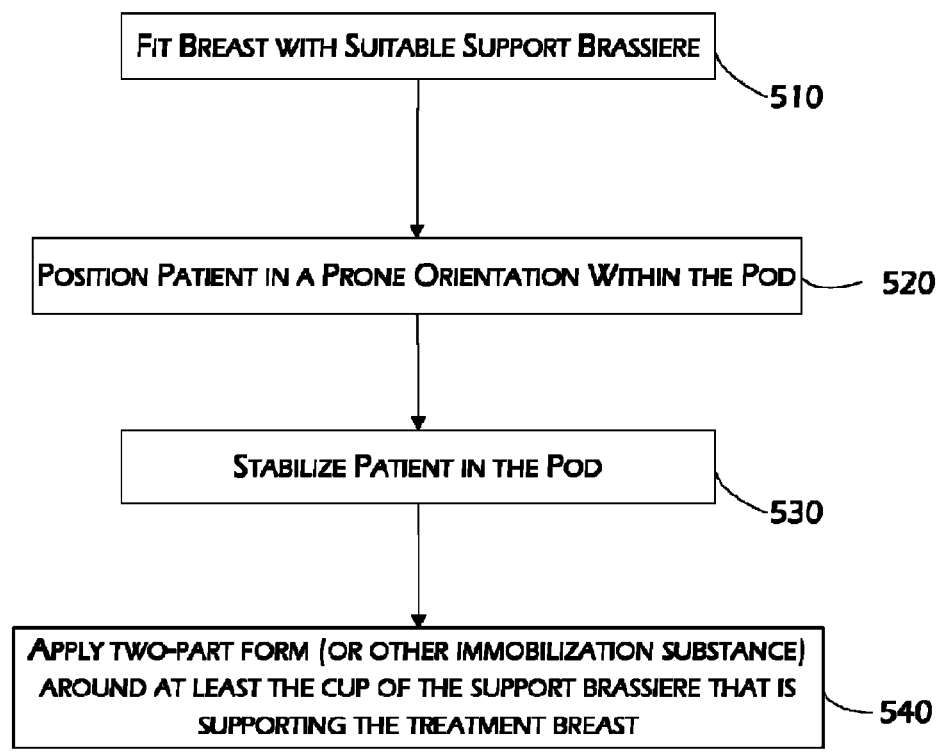
FIG. 5 is a flowchart illustrating an exemplary method of fabricating a breast immobilization device.

Beginning in block 410, a support structure having contours customized for immobilization of a particular patient is fabricated, such as according to the method of FIG. 5, for example. The breast immobilization device, such as the immobilization device 210, may be fitted in a pod or other support structure that support other regions of the patient.

Continuing to block 420, a treatment plan is developed for delivering radiation therapy to the patient. The radiation may be any type available for treatment, such as x-ray or proton therapy, for example. The developed treatment plan may include full breast or partial breast treatments. In one embodiment, because the breast immobilization device 210 provides reproducible immobilization of the patient's breast, the efficiency of the radiation therapy may be increased. Accordingly, use of the breast immobilization device 210 in treatment planning may reduce the time required for the actual radiation delivery to a lumpectomy, or other treatment region. In addition, the improved immobilization of the patient's breast, and the reduction of movement normally caused by breathing that is realized by placing a patient in a prone position, allows the treatment plan to reduce a target area of the breast and reduce the amount of tissue peripheral to the treatment region that receives radiation.

In certain embodiments, three-dimensional multi-beam proton treatment plans are developed. In one embodiment, the treatment plan calls for three to four separate axial treatment beams that are utilized with various beam weightings. For example, a proton beam may be utilized for treatments with appropriate apertures, compensators and beam modulation. In one embodiment, beams are chosen to provide complete sparing of underlying cardiac and pulmonary tissue as well as avoiding the breast that is not targeted for treatment. Care may also be taken to provide adequate skin sparing.

Figure 6:
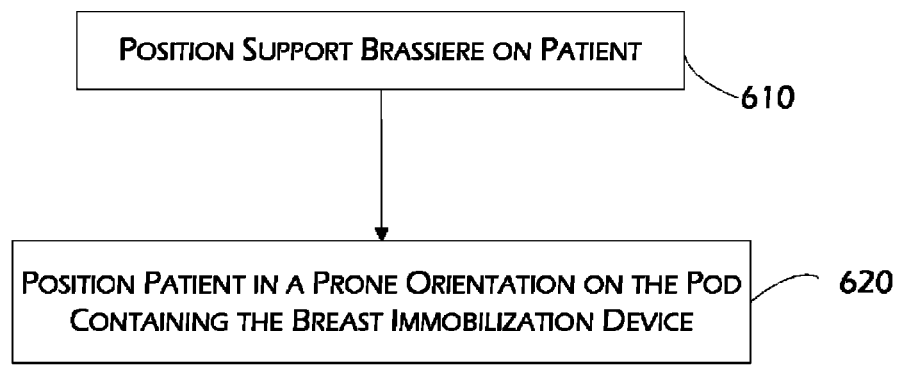
FIG. 6 is a flowchart illustrating an exemplary method of immobilizing a breast for radiation therapy.

Moving to block 430, the patient is immobilized for radiation treatment, such as according to the method of FIG. 6, for example. In one embodiment, the breast immobilization device fabricated in block 410, as well as a support structure in some embodiments, is used to reproducibly position the treatment breast in substantially the same position as when the treatment plan was developed. Because the breast immobilization device is solidified and formed to snugly engage the contours of the patients' breast (or the outer surface of a cup of the support brassiere), when the patient is positioned in the support structure the treatment breast is immobilized in substantially the same position as used when the breast immobilization device was fabricated. In embodiments where a support brassier is worn by the patient when the breast immobilization device is formed, the support brassier is again worn by the patient when the patient is immobilized for treatment.

Next, in block 440, radiation therapy, such as partial breast radiation therapy, is delivered to the patient. As noted above, any other type of radiation therapy may also be administered to the patient that is immobilized by the immobilization device.

Continuing to block 450, the administering physician, radiologist, or other personnel, determines if additional doses are to be delivered to the patient. In one embodiment, this determination is made primarily based on the predetermined treatment plan and may be made prior to fabrication of the immobilization device. For example, a radiation oncologist may prescribe a particular radiation dose on a periodic basis for a predetermined time period, such as every day for 2-6 weeks or once a week for several months. In some embodiments, the effects of the treatment are monitored and the treatment plan may be adjusted after certain radiotherapy treatments. If additional doses are to be applied, the method returns to block 430 where the patient is again immobilized and irradiation is applied to the immobilized breast (block 440). In one embodiment, the patient is fitted with the support brassiere, which may be reproducibly placed on the chest by utilizing applied skin marks. The patient may then be positioned in the breast immobilization device in a prone position on the support structure. In certain embodiments, orthogonal diagnostic quality x-rays are performed prior to each treatment and compared to digitally reconstructed radiographs to reproduce the body/breast position at the time of treatment planning CT scan. In certain embodiments, clips, such as titanium clips, which are placed at the periphery of the biopsy cavity or other anatomical locations may also be utilized for the alignment process.

Advantageously, the time period between sequential radiation treatments, and the associated immobilization of the patient, may vary significantly without affecting the reproducibility of immobilization that is obtained through using the breast immobilization device, and optionally the support brassier. For example, a patient treatment plan may call for daily, weekly, or monthly treatments. In any case, the patient is reproducibly immobilized using the breast immobilization device that is contoured to support the specific patient's breast in the prone position. As noted above, because the patient is placed in the prone position, the amount of breast movement caused by breathing may also be reduced, when compared to the amount of breast movement when in a supine position.

When no further treatment sessions are necessary, the method continues to block 450 where the treatment is complete.

FIG. 5 is a flowchart illustrating an exemplary method of fabricating a breast immobilization device, such as breast immobilization device 210. Depending on the embodiment, the method of FIG. 5 may include fewer or additional blocks and the blocks may be performed in a different order than is illustrated.

Beginning in block 510, the patient is fitted with a support brassier, such as the brassier illustrated in FIGS. 3A and 3B. In one embodiment, the support brassier comprises a rigid or semi-rigid cup that engages the treatment breast. The support brassier is configured so that the breasts may be repeatedly repositioned within the cup at substantially the same position. In some embodiments, a support brassier is not used in forming the immobilization device. In such an embodiment, a cup may be placed and/or held on the breast as the two-part foam is being poured around the breast and released prior to complete hardening of the two-part foam. In this embodiment, the cup may be part of the immobilization structure. In other embodiments, the patients skin may directly contact the two-part foam as the immobilization device is being formed.

Moving to block 520, the patient is positioned in a support structure, such as support structure 200 (FIG. 1), with a slight gap between the breasts and a bottom 205 of the pod 200. In other embodiments, however, the breasts may minimally contact the pod 200. If the breasts are compressed excessively, such as by having a portion of the patient's weight supported by the breasts compressed against the bottom of the pod 200, the breasts will be positioned closer to the patient's internal organs, such as heart and lungs. Additionally, accurate repositioning of the patient in a position where the breasts are compressed may be more difficult as the position of a particular breast region tends to vary from one compression of the breast to another. Accordingly, in an advantageous embodiment, the breasts are positioned with a small gap, or minimally contacting, the pod 200.

Continuing to block 530, the patient's shoulders, abdomen, and/or pelvis are supported by pillows, beanbags, foam structures, such as foam bead vacuum cushions, and/or other support structures, while leaving an area around the breasts temporarily directly unsupported. In this embodiment, the air may be removed from the vacuum cushions prior to placement of the two-part foam around the chest area (block 540), in order to provide a substantially rigid immobilization for the head, shoulder, abdomen, and/or pelvis areas. Thus, in certain embodiments the pod 200 is at least partially filled with one or more pillows, beanbags, foam structures, or similar materials. In certain embodiments, blocks 520 and 530 are performed concurrently, as the positioning of support structures around the patient aid in positioning of the patient's treatment breast in the appropriate positioned with respect to the pod 200.

Continuing to block 540, a two-part foam is poured around the chest region of the patient and allowed to harden around the breasts so that the contours of the breasts, or of the support brassier if used, are mirrored in negative relief in the hardened foam. More particularly, the two-part foam is initially malleable so that it may be poured around the chest of the patient and substantially fills the air spaces around the breasts (or brassiere). In one embodiment, the two-part form undergoes chemical changes that cause the foam to solidify. Accordingly, because the two-part form is placed around the breasts prior to solidifying, the foam will become a hardened mold of the patient's breasts, or of the support brassiere, when solidified in order to form the breast immobilization device. This breast immobilization device allows the breast to remain in a hanging position, rather than being compressed against a bottom surface of the pod 200. In one embodiment, rather than using two-part foam, the breast immobilization device may be formed of one or more foam bead vacuum cushion, or other materials that suitably conform to the contours of a patient's breast (and/or support brassiere) and provide a rigid or semi-rigid support structure.

FIG. 6 is a flowchart illustrating an exemplary method of immobilizing a breast for radiotherapy. As noted above, using the patient-specific breast immobilization device, a patient may be accurately and reproducibly positioned for delivery of radiation therapy, while simultaneously positioning the patient in a prone position so as to reduce respiratory motion. Depending on the embodiment, the method of FIG. 6 may include fewer or additional blocks and the blocks may be performed in a different order than is illustrated.

Beginning at block 610, the support brassier that was used to fabricate the breast immobilization device is repositioned on the patient. In one embodiment, the support brassiere is reproducibly placed on the chest of the patient utilizing applied skin marks. In other embodiments, other markers, such as small tattoos, for example, may be used to position the support brassier in substantially the same position on the patient as when the breast immobilization device was fabricated.

Moving to block 620, the patient is positioned in a prone position within the pod containing the breast immobilization device. In one embodiment, the patient lays on the pod containing the breast immobilization device so that the treatment breast is placed in the corresponding contour in the immobilization device. With the patient positioned on the pod, the pod may be moved to the radiation delivery area, such as within a gantry for radiotherapy.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A system for immobilizing a patient and a breast of the patient for delivery of radiation to the breast of the patient, the system comprising:
a support structure configured to support a patient lying in a substantially prone position such that a breast to be treated is located below the patient and above the support structure, the support structure further configured to allow the patient to relax and thereby maintain a stable and consistent position for delivery of radiation;
a brassiere comprising a cup and at least one strap configured to be worn by the patient, the cup configured to at least partially contain the breast to be treated; and
a breast immobilization device comprising a non-caustic substance configurable to at least partially and dynamically fill the space between the brassiere and the support structure, forming, in negative relief, contours corresponding to at least a portion of the cup having the breast to be treated, the breast immobilization device configurable to be positioned on the support structure generally beneath the patient and supporting the cup and the breast to be treated;
wherein the non-caustic substance has a first, more expandable state and a second, less expandable state, the first state allowing the non-caustic substance to be introduced into the space between the cup and the support structure, and the second state allowing the non-caustic substance to generally support and retain the breast and cup, thereby substantially immobilizing the breast for radiation treatment.

2. The system of claim 1, wherein the first, more expandable state of the non-caustic substance is also a more fluid state and the second, less expandable state of the non-caustic substance is also a less fluid state.

3. The system of claim 2, wherein the non-caustic substance is formed from at least two fluids that do not react when stored separately, the fluids configured to be mixed together to thereby react and create a foam that expands and hardens into the general shape of a cavity into which they are introduced as or shortly after they are mixed together.

4. A system for immobilizing a patient and a breast for delivery of radiation to a breast of the patient, the device comprising:

a support structure configured to support a patient's body face down such that a breast to be treated is suspended above the support structure;

a brassiere comprising a cup and at least one strap configured to be worn by the patient, the cup configured to at least partially contain the breast to be treated; and a breast immobilization device comprising a substance configured to at least partially fill the space between the brassiere and the support structure and to have contours corresponding to a negative relief image of at least a portion of the brassiere, the breast immobilization device configured to be positioned on the support structure generally beneath the patient and supporting the brassiere and the breast to be treated.

5. The system of claim 4, wherein the cup comprises a portion of the brassiere that is configurable to be releasably secured to the patient.

6. The system of claim 4, wherein the system is configured for positioning the patient for delivery of radiation through the support structure, through the brassiere, and through the breast immobilization device to a target area within the breast.

7. The system of claim 6, wherein the support structure, the brassiere, and the breast immobilization device are all formed from substances that allow radiation to pass through them without substantial reflection or scattering of the radiation.

8. The system of claim 4, wherein the support structure comprises a table having sides configured to contain the breast immobilization device and prevent it from sliding.

9. The system of claim 8, wherein the support structure comprises a pod.

10. The system of claim 4, wherein the breast immobilization device is custom-formed for engagement with the cup as it is oriented on the breast of the patient for treatment delivery.

* * * * *

UNITED STATES PATENT AND TRADEMARK OFFICE
CERTIFICATE OF CORRECTION

PATENT NO.         : 8,523,630 B2                              Page 1 of 1
APPLICATION NO.    : 13/540475
DATED              : September 3, 2013
INVENTOR(S)        : Bush It is certified that error appears in the above-identified patent and that said Letters Patent is hereby corrected as shown below:

In the Specification

In column 2 at line 30, change "treatment" to --treatment.--.

In column 2 at line 50, change "throughout" to --throughout.--.

In column 6 at line 67, change "2C," to --2B,--.

In column 7 at line 4, change "2C," to --2B,--.

In column 8 at line 55, change "38." to --3B.--.

Signed and Sealed this
Eighth Day of April, 2014

Michelle K. Lee
*Deputy Director of the United States Patent and Trademark Office*